US008568862B2

(12) United States Patent
Ogawa

(10) Patent No.: US 8,568,862 B2
(45) Date of Patent: Oct. 29, 2013

(54) PATTERNED FINE PARTICLE FILM STRUCTURES

(75) Inventor: Kazufumi Ogawa, Awa (JP)

(73) Assignee: Empire Technology Development LLC, Wilmington, DE (US)

(\*) Notice: Subject to any disclaimer, the term of this patent is extended or adjusted under 35 U.S.C. 154(b) by 550 days.

(21) Appl. No.: 12/530,553

(22) PCT Filed: Mar. 7, 2008

(86) PCT No.: PCT/JP2008/054215
§ 371 (c)(1),
(2), (4) Date: Feb. 11, 2010

(87) PCT Pub. No.: WO2008/111536
PCT Pub. Date: Sep. 18, 2008

(65) Prior Publication Data
US 2010/0143665 A1 Jun. 10, 2010

(30) Foreign Application Priority Data
Mar. 9, 2007 (JP) .................. 2007-060548

(51) Int. Cl.
*B32B 3/10* (2006.01)
(52) U.S. Cl.
USPC ........... 428/195.1; 556/465; 549/215; 525/50
(58) Field of Classification Search
USPC ................................. 428/195.1
See application file for complete search history.

(56) References Cited

U.S. PATENT DOCUMENTS

| 6,420,086 B1 | 7/2002 | Yang et al. |
| 6,805,904 B2 | 10/2004 | Anders et al. |
| 2005/0048414 A1* | 3/2005 | Harnack et al. ............... 430/322 |
| 2006/0177855 A1* | 8/2006 | Utermohlen et al. ............ 435/6 |

FOREIGN PATENT DOCUMENTS

| JP | 11-066654 | 3/1999 |
| JP | 11-350153 A | 12/1999 |
| JP | 2001-184620 A | 7/2001 |
| JP | 2003-168606 A | 6/2003 |
| JP | 2007-118276 A | 5/2007 |

OTHER PUBLICATIONS

Epoxy Layered Silicate Nanocomposites, Becker et al., Adv. Polym. Sci. 2005, 179: 29-82.*
International Search Report and Written Opinion from International Application No. PCT/JP2008/054215 mailed May 20, 2008.

(Continued)

*Primary Examiner* — Mark Ruthkosky
*Assistant Examiner* — Ian Rummel
(74) *Attorney, Agent, or Firm* — Workman Nydegger

(57) ABSTRACT

A patterned fine particle film structure includes a fine particle layer including fine particles arranged and bound to a surface of a substrate coated with a patterned film including a first film compound having a first functional group. The fine particles are coated with films including a first coupling agent having a first coupling reactive group that undergoes a coupling reaction with the first functional group to form a bond. The fine particle layer is bound by a bond formed through a coupling reaction. In an embodiment, fine particles coated with films of a film compound that reacts with the first coupling reactive group and the fine particles are alternately bound to the substrate.

10 Claims, 5 Drawing Sheets

WHERE ● INDICATED BY (A) REPRESENTS 2-METHYLIMIDAZOLE

(56) References Cited

OTHER PUBLICATIONS

"Self-assembled monolayer," accessed at http://en.wikipedia.org/wiki/Self-assembled_monolayer, last modified Apr. 18, 2013, pp. 11.

Fan, H., et al., "Rapid prototyping of patterned functional nanostructures," Nature, vol. 405, pp. 56-60, Macmillan Magazines Ltd (2000).

Ghosh, P., et al., "Two New Approaches for Patterning Polymer Films Using Templates Prepared by Microcontact Printing," Macromolecules, vol. 34, Issue 5, pp. 1230-1236, American Chemical Society (2001).

Tan, N., et al., "Imprinting polymer film on patterned substrates," Journal of Vacuum Science & Technology B: Microelectronics and Nanometer Structures, vol. 21, Issue 6, pp. 2742-2748, American Vacuum Society (2003).

* cited by examiner (A)

(B)

WHERE ⬮ INDICATED BY (A) REPRESENTS 2-METHYLIMIDAZOLE (A)

(B)

WHERE ● INDICATED BY (A) REPRESENTS 2-METHYLIMIDAZOLE (A)

(B)

(A)

WHERE (B)

WHERE

US 8,568,862 B2

PATTERNED FINE PARTICLE FILM STRUCTURES

TECHNICAL FIELD

Embodiments described herein relate to patterned films of fine particles.

BACKGROUND

The Langmuir-Blodgett (LB) technique using amphiphilic organic molecules is conventionally known, in which the molecules are arranged over a water surface to deposit a monomolecular film on a surface of a substrate. Also known is chemical adsorption (CA), in which a monomolecular film is deposited by chemical adsorption in a solution containing a surfactant.

BRIEF DESCRIPTION OF THE FIGURES

FIG. 3(A) shows the sectional structure of an unreacted glass substrate; and

FIG. 3(B) shows the sectional structure of a glass substrate on which a monomolecular film of a film compound having an epoxy group is formed.

FIG. 5(A) shows the sectional structure of an unreacted fine nickel particle; and FIG. 5(B) shows the sectional structure of a fine nickel particle on which a monomolecular film of a film compound having an epoxy group is formed.

DETAILED DESCRIPTION

Figure 1:
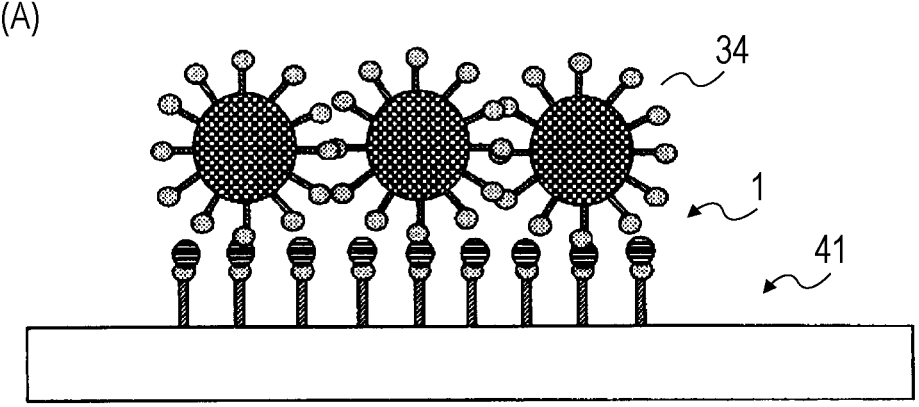
FIG. 1(A) is an illustrative diagram schematically showing the sectional structure of a patterned single-layer fine particle film according to a first embodiment.
FIG. 1(B) is an illustrative diagram schematically showing the sectional structure of a patterned multilayer fine particle film according to the same embodiment.
Figure 1:
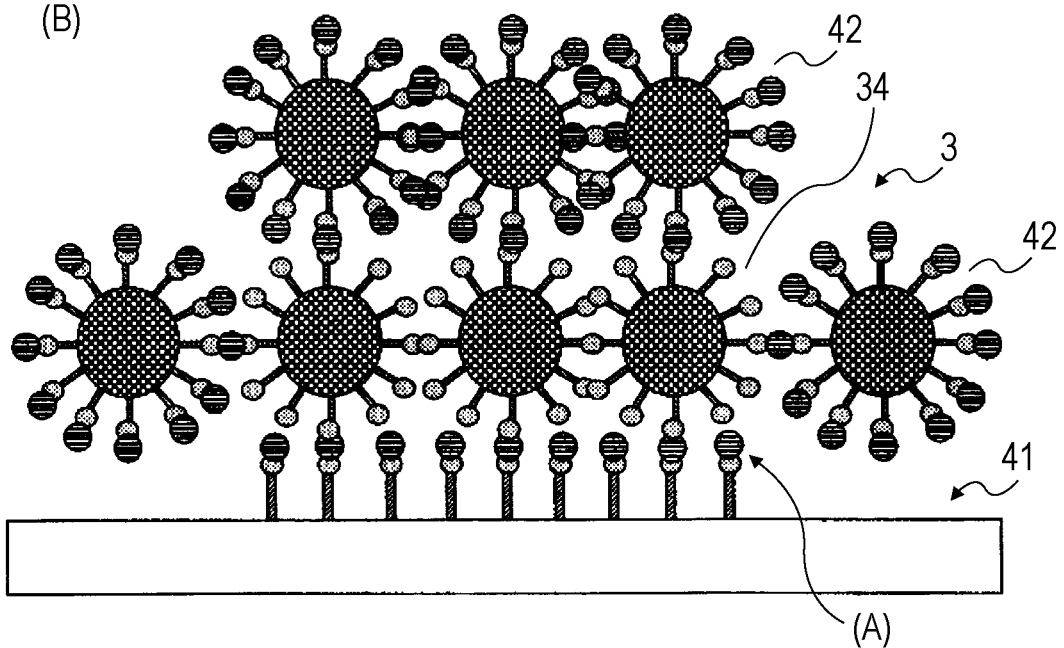

Referring to FIGS. 1(A) and 1(B), a patterned single-layer fine particle film 1 and a patterned multilayer fine particle film 3 according to the first embodiment will be described. The patterned single-layer fine particle film 1 and the patterned multilayer fine particle film 3 each includes a fine particle layer in which epoxidized fine nickel particles (an example of first coated fine particles) 34 are arranged and bound to a surface of a reactive glass substrate (an example of a reactive substrate) 41.

In the patterned multilayer fine particle film 3, as shown in FIG. 1(B), the first to nth fine particle layers (where n is an integer of two or more; n=2 in this embodiment) are sequentially stacked in order from the reactive glass substrate 41 side to the air interface side.

The surface of the reactive glass substrate 41 is coated with a monomolecular film 13 (see FIG. 3(B)) of a film compound having an epoxy group (an example of a first film compound) and is further coated with a film of 2-methylimidazole (an example of a first coupling agent) bound by a bond formed through a coupling reaction between an amino group (an example of a first coupling reactive group) of 2-methylimidazole and the epoxy group.

The surfaces of reactive fine nickel particles 42 forming a second fine particle layer are further coated with films of 2-methylimidazole (an example of a third coupling agent) bound by a bond formed through a coupling reaction between an amino group (an example of a third coupling reactive group) of 2-methylimidazole and an epoxy group.

The reactive glass substrate 41 and the epoxidized fine nickel particles 34 forming the first fine particle layer are bound to each other by a bond formed through a coupling reaction between the epoxy group and the amino or imino group of 2-methylimidazole. Similarly, the epoxidized fine nickel particles 34 forming the first fine particle layer and the reactive fine nickel particles 42 forming the second fine particle layer are bound to each other.

As shown in FIG. 1(B), the reactive fine nickel particles 42 can also be bound to the sides of the epoxidized fine nickel particles 34 of the first layer. It is noted that FIG. 1(B) is drawn with the size of the fine particles exaggerated relative to that of the actual pattern for illustration purposes.

Referring to FIGS. 3(A), 3(B), 4(A), 5(A), and 5(B), methods for producing the patterned single-layer fine particle film 1 and the patterned multilayer fine particle film 3 according to various embodiments are disclosed. The method includes a step A (see FIG. 3) of preparing an epoxidized glass substrate 14 (an example of a coated substrate) by bringing a solution containing an alkoxysilane compound having an epoxy group (an example of a first film compound) into contact with a surface of a glass substrate (an example of a substrate) 11 to form a bond between alkoxysilyl groups (an example of a first binding group) and hydroxyl groups 12 on the surface of the glass substrate 11. The method further includes a step B (see FIG. 4) of preparing a patterned epoxidized glass substrate 22 or 24 through patterning treatment in which the surface of the epoxidized glass substrate 14 is subjected to light irradiation (an example of energy irradiation) through a mask 21 covering a pattern region so that the epoxy group is left only in the pattern region. The method also includes a step C (see FIG. 5) of preparing the epoxidized fine nickel particles 34 by bringing an alkoxysilane compound having an epoxy group (an example of a second film compound) into contact with the surfaces of fine nickel particles (an example of fine particles) 31 to form a bond between alkoxysilyl groups (an example of a second binding group) and hydroxyl groups 31 on the surfaces of the fine nickel particles 31. The method additionally includes a step D of preparing the reactive glass substrate 41 (see FIGS. 1(A) and 1(B)) by bringing 2-methylimidazole into contact with the surface of the patterned epoxidized glass substrate 22 (see FIG. 4) to facilitate a coupling reaction between the epoxy group and an amino group, and then binding the epoxidized fine nickel particles 34 to the surface of the reactive glass substrate 41 by bringing the epoxidized fine nickel particles 34 into contact with the surface of the reactive glass substrate 41 to form a bond through a coupling reaction between the epoxy group and an imino group (an example of a second coupling reactive group), followed by removing unbound epoxidized fine nickel particles 34.

In step E the epoxidized fine nickel particles (an example of second coated fine particles) 34 are prepared by bringing a solution containing an epoxidized alkoxysilane compound (an example of a third film compound) into contact with the surfaces of the fine nickel particles 31 to form a bond between alkoxysilyl groups (an example of a third binding group) and hydroxyl groups 32 on the surfaces of the fine nickel particles 31, and then preparing the reactive fine nickel particles (an example of second reactive fine particles) 42 by bringing 2-methylimidazole (an example of a second coupling agent) into contact with the surfaces of the epoxidized fine nickel particles 34 so that they have films including 2-methylimidazole bound to the surfaces thereof by a bond formed through a coupling reaction between the epoxy group (an example of a third functional group) and an amino group. In a step F the reactive fine nickel particles 42 are bound to the fine particle layer of the epoxidized fine nickel particles 34 by bringing the reactive fine nickel particles 42 into contact with the surface of the patterned single-layer fine particle film 1 or the patterned multilayer fine particle film 3, which includes the fine particle layer of the epoxidized fine nickel particles 34, to form a bond through a coupling reaction between the epoxy group and the imino group, followed by removing unbound reactive fine nickel particles 42. In step G the epoxidized fine nickel particles 34 are bound to the fine particle layer of the reactive fine nickel particles 42 by bringing the epoxidized fine nickel particles 34 into contact with the surface of the patterned multilayer fine particle film 3, which includes the fine particle layer of the reactive fine nickel particles 42, to form a bond through a coupling reaction between the epoxy group and the imino group, followed by removing unbound epoxidized fine nickel particles 34.

he steps A to G will now be described in more detail below. Referring to FIGS. 3(A) and 3(B), in the step A, a film compound having an epoxy group is brought into contact with the glass substrate 11 to produce the epoxidized glass substrate 14, with its surface coated with the monomolecular film 13 of the film compound having an epoxy group. The size of the glass substrate 11 is not particularly limited.

Any compound that can be adsorbed or bound to the surface of the glass substrate 11 to form a self-assembled monomolecular film may be used as the film compound having an epoxy group. One example is an alkoxysilane compound having a functional group including an epoxy group (oxirane ring) at one terminal of a linear alkylene group and an alkoxysilyl group (an example of a first binding group) at the other terminal, as represented by the following general formula (Chemical Formula 1).

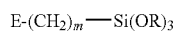

Chemical Formula 1

In the above formula, the functional group E denotes the functional group including an epoxy group, m denotes an integer of 3 to 20, and R denotes an alkyl group having one to four carbon atoms.

Specific examples of the film compound, having an epoxy group, that can be used include the alkoxysilane compounds shown in Items (1) to (12) below.

(1) $(CH_2OCH)CH_2O(CH_2)_3Si(OCH_3)_3$
(2) $(CH_2OCH)CH_2O(CH_2)_7Si(OCH_3)_3$
(3) $(CH_2OCH)CH_2O(CH_2)_{11}Si(OCH_3)_3$
(4) $(CH_2CHOCH(CH_2)_2)CH(CH_2)_2Si(OCH_3)_3$
(5) $(CH_2CHOCH(CH_2)_2)CH(CH_2)_4Si(OCH_3)_3$
(6) $(CH_2CHOCH(CH_2)_2)CH(CH_2)_6Si(OCH_3)_3$
(7) $(CH_2OCH)CH_2O(CH_2)_3Si(OC_2H_5)_3$
(8) $(CH_2OCH)CH_2O(CH_2)_7Si(OC_2H_5)_3$
(9) $(CH_2OCH)CH_2O(CH_2)_{11}Si(OC_2H_5)_3$
(10) $(CH_2CHOCH(CH_2)_2)CH(CH_2)_2Si(OC_2H_5)_3$
(11) $(CH_2CHOCH(CH_2)_2)CH(CH_2)_4Si(OC_2H_5)_3$
(12) $(CH_2CHOCH(CH_2)_2)CH(CH_2)_6Si(OC_2H_5)_3$

Herein the $(CH_2OCH)CH_2O-$ group denotes the functional group (glycidyl group) represented by Chemical Formula 2, and the $(CH_2CHOCH(CH_2)_2)CH-$ group denotes the functional group (3,4-epoxycyclohexyl group) represented by Chemical Formula 3.

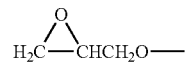

Chemical Formula 2

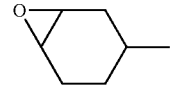

Chemical Formula 3

The epoxidized glass substrate 14 is produced by applying to the surface of the glass substrate 11 a reaction solution containing an alkoxysilane compound having an epoxy group and an alkoxysilyl group (an example of a second binding group), a condensation catalyst for promoting a condensation reaction between alkoxysilyl groups and the hydroxyl groups 12 on the surface of the glass substrate 11, and a nonaqueous organic solvent, and reacting them in air at room temperature. The application of the reaction solution may be performed by any method, such as doctor-blade coating, dip coating, spin coating, spraying, or screen printing.

The condensation catalyst used may be a metal salt, such as a metal carboxylate salt, a metal carboxylate ester salt, a metal carboxylate salt polymer, a metal carboxylate salt chelate, a titanate ester, or a titanate ester chelate.

The amount of condensation catalyst added may be 0.2% to 5% by mass, more specifically 0.5% to 1% by mass, of the amount of alkoxysilane compound.

Specific examples of metal carboxylate salts include stannous acetate, dibutyltin dilaurate, dibutyltin dioctoate, dibutyltin diacetate, dioctyltin dilaurate, dioctyltin dioctoate, dioctyltin diacetate, stannous dioctanoate, lead naphthenate, cobalt naphthenate, and iron 2-ethylhexanoate.

Specific examples of metal carboxylate ester salts include dioctyltin bisoctylthioglycolate ester salt and dioctyltin maleate ester salt.

Specific examples of metal carboxylate salt polymers include dibutyltin maleate salt polymer and dimethyltin mercaptopropionate salt polymer.

Specific examples of metal carboxylate salt chelates include dibutyltin bisacetylacetate and dioctyltin bisacetyllaurate.

Specific examples of titanate esters include tetrabutyl titanate and tetranonyl titanate.

Specific examples of titanate ester chelates include bis(acetylacetonyl)di-propyltitanate.

The alkoxysilyl groups undergo a condensation reaction with the hydroxyl groups 12 on the surface of the glass substrate 11 to form the monomolecular film 13 of the film compound having an epoxy group, which has the structure represented by Chemical Formula 4 below. The three single bonds extending from the oxygen atoms bind to the surface of the glass substrate 11 or to the adjacent silicon (Si) atoms of the silane compound, at least one of the bonds binding to a silicon atom on the surface of the glass substrate 11.

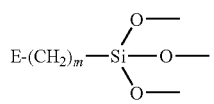

Chemical Formula 4

The reaction may be facilitated in air at a relative humidity of 45% or less because the alkoxysilyl groups decompose in the presence of water. In addition, since the condensation reaction is inhibited by oil and water on the surface of the glass substrate 11, such impurities are preferably removed in advance by sufficiently cleaning and drying the glass substrate 11.

If the condensation catalyst used is one of the above metal salts, it takes about two hours to complete the condensation reaction.

If one or more compounds selected from the group consisting of ketimine compounds, organic acids, aldimine compounds, enamine compounds, oxazolidine compounds, and aminoalkylalkoxysilane compounds are used as the condensation catalyst instead of the above metal salts, the reaction time can be reduced to about ½ to ⅔.

Alternatively, if these compounds are used as a cocatalyst and mixed with the above metal salts (they can be used in a mass ratio of 1:9 to 9:1, although about 1:1 is preferred), the reaction time can be further reduced.

If, for example, the epoxidized fine nickel particles 21 are produced using H3, a ketimine compound manufactured by Japan Epoxy Resins Co., Ltd., as the condensation catalyst instead of dibutyltin oxide, with the other conditions being identical, the reaction time can be reduced to about one hour without impairing the quality of the epoxidized fine nickel particles 21.

In addition, if the epoxidized fine nickel particles 21 are produced using a mixture of H3 from Japan Epoxy Resins Co., Ltd. and dibutyltin bisacetylacetonate (in a mixing ratio of 1:1) as the condensation catalyst, with the other conditions being identical, the reaction time can be reduced to about 20 minutes.

Examples of ketimine compounds that can be used include, but not limited to, 2,5,8-triaza-1,8-nonadiene, 3,11-dimethyl-4,7,10-triaza-3,10-tridecadiene, 2,10-dimethyl-3,6,9-triaza-2,9-undecadiene, 2,4,12,14-tetramethyl-5,8,11-triaza-4,11-pentadecadiene, 2,4,15,17-tetramethyl-5,8,11,14-tetraaza-4,14-octadecadiene, and 2,4,20,22-tetramethyl-5,12,19-triaza-4,19-trieicosadiene.

Examples of organic acids that can be used include, but not limited to, formic acid, acetic acid, propionic acid, butyric acid, and malonic acid.

The reaction solution can be produced using an organochlorine solvent, a hydrocarbon solvent, a fluorocarbon solvent, a silicone solvent, or a mixed solvent thereof. To prevent hydrolysis of the alkoxysilane compound, water is preferably removed from the solvent used with a desiccant or by distillation. In addition, the boiling point of the solvent may be 50° C. to 250° C.

Specific examples of solvents that can be used include nonaqueous solvents such as petroleum naphtha, solvent naphtha, petroleum ether, petroleum benzin, isoparaffin, normal paraffin, decalin, industrial gasoline, nonane, decane, kerosene, dimethyl silicone, phenyl silicone, alkyl-modified silicone, polyether silicone, and dimethylformamide.

In addition, alcohol solvents such as methanol, ethanol, and propanol or mixtures thereof can be used.

In addition, examples of fluorocarbon solvents that can be used include chlorofluorocarbon solvents, Fluorinert (manufactured by 3M Company of the United States), and Aflude (manufactured by Asahi Glass Co., Ltd.). These solvents may be used alone or in combination of two or more if they are sufficiently miscible with each other. In addition, an organochlorine solvent such as dichloromethane or chloroform may be added.

The concentration of the alkoxysilane compound in the reaction solution may be 0.5% to 3% by mass.

After the reaction, the glass substrate 11 is cleaned with a solvent to remove excess alkoxysilane compound and condensation catalyst remaining unreacted on the surface thereof, so that the epoxidized glass substrate 14 is obtained, with its surface coated with the monomolecular film 13 of the film compound having an epoxy group. FIG. 3(B) shows a schematic diagram of the sectional structure of the epoxidized glass substrate 14 thus produced.

The cleaning solvent used may be any solvent that can dissolve the alkoxysilane compound. For example, dichloromethane, chloroform, and N-methylpyrrolidone are cleaning solvents that are inexpensive, are highly capable of dissolving the alkoxysilane compound, and can readily be removed by air drying.

If the resultant epoxidized glass substrate 14 is left in air without being cleaned with a solvent after the reaction, some of the alkoxysilane compound remaining on the surface thereof is hydrolyzed by water in air to form silanol groups, which undergo a condensation reaction with the alkoxysilyl groups. As a result, an ultrathin polymer film of polysiloxane is formed on the surface of the epoxidized glass substrate 14. Although not necessarily being covalently bound to the surface of the epoxidized glass substrate 14, the polymer film, having epoxy groups, displays the same reactivity as the monomolecular film 13 of the film compound having an epoxy group for the epoxidized glass substrate 14. Even without cleaning, therefore, no problem arises in the step C and the subsequent production process.

While an alkoxysilane compound having an epoxy group is used in this embodiment, an alkoxysilane compound having an amino group at one terminal of a linear alkylene group and an alkoxysilyl group at the other terminal may also be used, as represented by the following general formula (Chemical Formula 5).

A compound having glycidyl groups at either terminal thereof can be used as a coupling agent that reacts with an amino or imino group.

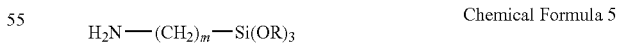

Chemical Formula 5

In the above formula, m denotes an integer of 3 to 20, and R denotes an alkyl group having one to four carbon atoms. Specific examples of the film compound, having an amino group, that can be used include the alkoxysilane compounds shown in Items (21) to (28) below.

(21) $H_2N(CH_2)_3Si(OCH_3)_3$
(22) $H_2N(CH_2)_5Si(OCH_3)_3$
(23) $H_2N(CH_2)_7Si(OCH_3)_3$
(24) $H_2N(CH_2)_9Si(OCH_3)_3$
(25) $H_2N(CH_2)_5Si(OC_2H_5)_3$

(26) H$_2$N(CH$_2$)$_5$Si(OC$_2$H$_5$)$_3$
(27) H$_2$N(CH$_2$)$_7$Si(OC$_2$H$_5$)$_3$
(28) H$_2$N(CH$_2$)$_9$Si(OC$_2$H$_5$)$_3$

In this case, however, among condensation catalysts that can be used for the reaction solution, compounds containing tin (Sn) salts cannot be used as the condensation catalyst for an alkoxysilane compound having an amino group because they react with an amino group to form a precipitate.

If an alkoxysilane compound having an amino group is used, the same compounds, excluding tin carboxylate salts, tin carboxylate ester salts, tin carboxylate salt polymers, and tin carboxylate salt chelates, as used for an alkoxysilane compound having an epoxy group can be used as the condensation catalyst alone or as a mixture of two or more.

The type and combination of cocatalyst that can be used, the type of solvent, the concentrations of the alkoxysilane compound, the condensation catalyst, and the cocatalyst, the reaction conditions, and the reaction time are similar to those for an alkoxysilane compound having an epoxy group, and a description thereof will therefore be omitted.

While a glass substrate is used as the substrate in this embodiment, an optical device such as a lens or a diffraction grating may also be used as the substrate.

An alkoxysilane compound may also be used as the film compound if the substrate has active hydrogen groups, such as hydroxyl groups or amino groups, on its surface. Specific examples of such a substrate include metal foil and metal plates such as copper plates, aluminum plates, and silicon wafers. Accordingly, a member including such a substrate as a component may also be used as the substrate, as exemplified by electronic components such as semiconductor wafers and printed boards and various mechanical components such as micromachines.

While the film compound used in this embodiment is a silane compound that undergoes a condensation reaction with the active hydrogen groups on the surface of the substrate, the film compound used may also be, for example, a thiol or triazinethiol derivative, which forms a strong bond with a gold atom, if a substrate having a gold plating layer is used, as in the step A.

While the film compound used in this embodiment is a silane compound that undergoes a condensation reaction with the active hydrogen groups on the surfaces of the fine particles, the film compound used may also be, for example, a thiol or triazinethiol derivative, which forms a strong bond with a gold atom, if fine gold particles or a substrate having a gold plating layer is used.

Referring to FIG. 4(A), in the step B, the patterning treatment is performed by exposing the surface of the epoxidized glass substrate 14 through the mask 21 covering the pattern region to prepare the patterned epoxidized glass substrate 22, with the epoxy group selectively left only in the pattern region.

The mask used for the exposure may be formed of any material that is not transparent or damaged by irradiation light at least during the exposure. For example, the mask may be made from a material used for reticles employed in photolithography in the production of, for example, semiconductor devices. The exposure may be full-size exposure or may be reduced projection exposure if, for example, a fine pattern is formed.

The light source used may be laser light from, for example, an excimer laser such as a XeF (353 nm) laser, a XeCl (308 nm) laser, a KrF (248 nm) laser, or an ArF (193 nm) laser. Referring to FIG. 4(A), irradiation with laser light raises the temperature in an irradiated region, thereby removing the film compound having an epoxy group that covers the irradiated region (23), so that the patterned epoxidized glass substrate 22 is obtained (see FIG. 4(B)).

To prevent heat transfer to the region other than the irradiated region, the epoxidized film compound is preferably removed by pulse laser ablation using a pulse laser.

The intensity of the laser light may be 0.1 to 0.3 J·cm$^{-2}$. If the intensity of the laser light falls below 0.1 J·cm$^{-2}$, the film compound having an epoxy group cannot be sufficiently removed, and if the intensity exceeds 0.3 J·cm$^{-2}$, the glass portion of the epoxidized glass substrate 14 is removed.

If the intensity of the laser light falls within the above range, the pulse width may be 5 to 50 ns.

While the epoxidized film compound is removed by pulse laser ablation in the above embodiment, another type of energy irradiation, such as electron beam irradiation or X-ray irradiation, may be employed. In addition, instead of exposure through a mask, the epoxidized film compound may be removed from the region other than the pattern by selectively drawing the pattern directly on the epoxidized glass substrate 14 with, for example, an electron beam.

Referring to FIG. 4(B), in a step of performing patterning treatment according to an embodiment, the patterned epoxidized glass substrate 24 is prepared by applying a photopolymerization initiator to the surface of the epoxidized glass substrate 14 and exposing the surface of the epoxidized glass substrate 14 through the mask 21 covering the pattern region to facilitate a ring-opening polymerization of the epoxy group in the exposed region so that the epoxy group is left only in the pattern region.

The photopolymerization initiator that can be used may be, for example, a cationic photopolymerization initiator such as a diaryliodonium salt. The light source used may be, for example, a high-pressure mercury lamp or a xenon lamp.

Figure 5:
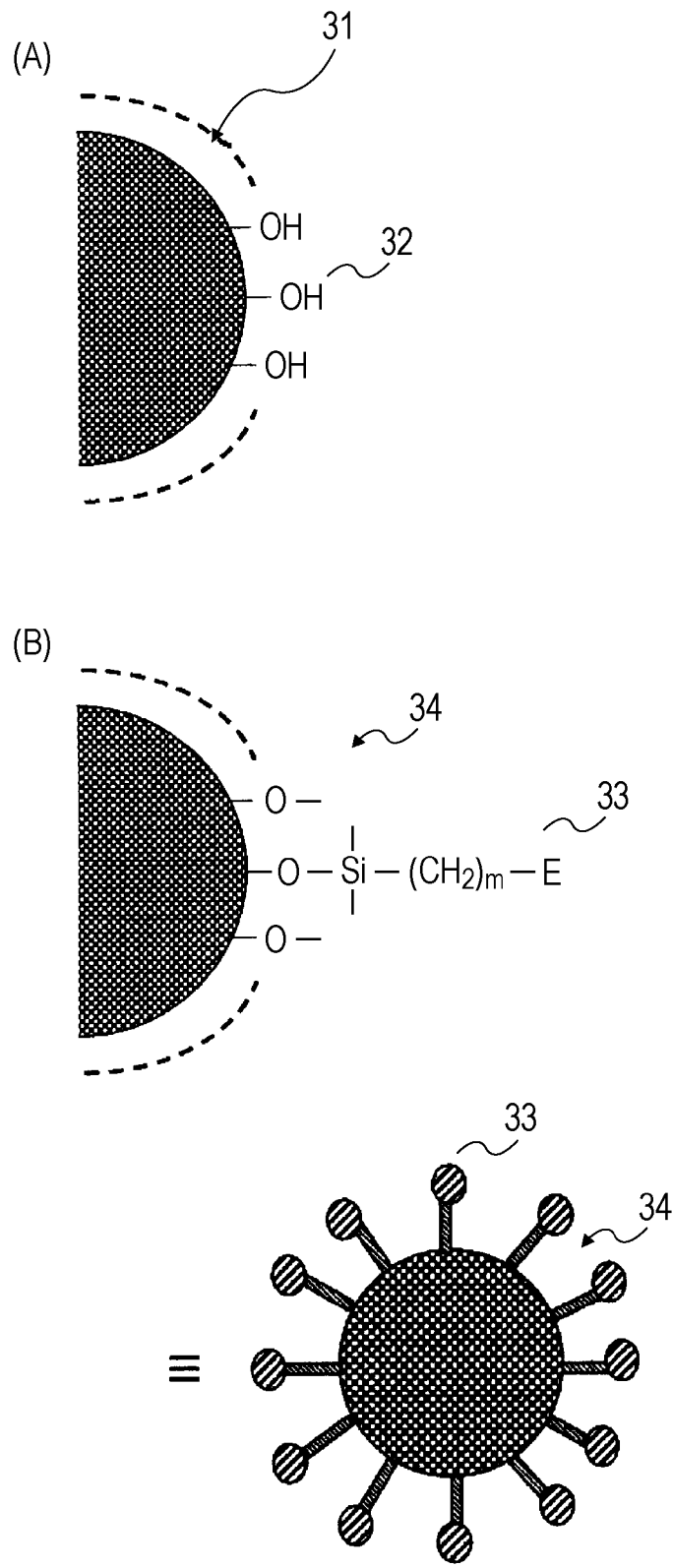
FIGS. 5(A) and 5(B) are a set of conceptual diagrams, enlarged to the molecular level, illustrating a step of producing epoxidized fine nickel particles in the methods for producing the patterned fine particle films.

In the step C, a film compound having an epoxy group similar to that used in the step A is brought into contact with the fine nickel particles 31 to produce the epoxidized fine nickel particles 34, with their surfaces coated with monomolecular films 33 of the film compound having an epoxy group (see FIG. 5).

The size of the fine nickel particles 31 may be, but is not limited to, 10 nm to 0.1 mm. If the size of the fine nickel particles 31 falls below 10 nm, the effect of the molecular size of the film compound is no longer negligible. If the particle size exceeds 0.1 mm, the mass of the fine nickel particles 31 is so large relative to their surface area that they cannot be supported after a coupling reaction.

The epoxidized fine nickel particles 34 are produced by dispersing the fine nickel particles 31 in a reaction solution containing an alkoxysilane compound having an epoxy group, a condensation catalyst for promoting a condensation reaction between alkoxysilyl groups and the hydroxyl groups 32 on the surfaces of the fine nickel particles 31, and a non-aqueous organic solvent, and reacting them in air at room temperature.

The type of alkoxysilane compound, having an epoxy group, that can be used in the step C, the types and combination of condensation catalyst and cocatalyst, the type of solvent, the concentrations of the alkoxysilane compound, the condensation catalyst, and the cocatalyst, the reaction conditions, and the reaction time are similar to those of the step A, and a description thereof will therefore be omitted.

After the reaction, the fine nickel particles 31 are cleaned with a solvent to remove excess alkoxysilane compound and condensation catalyst remaining unreacted on the surfaces thereof so that the epoxidized fine nickel particles 34 are obtained, with their surfaces coated with the monomolecular films 33 of the film compound having an epoxy group. FIG.

5(B) shows a schematic diagram of the sectional structure of the epoxidized fine nickel particles 34 thus produced.

The cleaning solvent used may be the same cleaning solvent as used in the step A.

If the resultant epoxidized fine nickel particles 34 are left in air without being cleaned with a solvent after the reaction, some of the alkoxysilane compound remaining on the surfaces thereof is hydrolyzed by water in air to form silanol groups, which undergo a condensation reaction with the alkoxysilyl groups. As a result, ultrathin polymer films of polysiloxane are formed on the surfaces of the epoxidized fine nickel particles 34. Although not being covalently bound to the surfaces of the epoxidized fine nickel particles 34, the polymer films, having epoxy groups, display the same reactivity as the monomolecular films 33 of the film compound having an epoxy group for the epoxidized fine nickel particles 34. Even without cleaning, therefore, no problem arises in the step D and the subsequent production process.

While an alkoxysilane compound having an epoxy group is used in this embodiment, an alkoxysilane compound having an amino group at one terminal of a linear alkylene group and an alkoxysilyl group at the other terminal may also be used, as in the step A.

In addition, while the alkoxysilane compound used in this embodiment is the same as that used in the step A, a different alkoxysilane compound may also be used. In that case, the alkoxysilane compound must have a functional group that reacts and forms a bond with a coupling reactive group of the coupling agent used in the step D.

While fine nickel particles are used as the fine particles in this embodiment, other inorganic fine particles, organic fine particles, or organic-inorganic hybrid fine particles may be used. In an alternative embodiment, organic and inorganic fine particles may be alternately stacked.

The term "inorganic fine particles" encompasses conductive fine particles, semiconductor fine particles, insulating fine particles, magnetic fine particles, fluorescent fine particles, light-absorbing fine particles, light-transmitting fine particles, and fine pigment particles. The term "organic fine particles" encompasses organic fluorescent fine particles, organic light-absorbing fine particles, organic light-transmitting fine particles, organic pigment fine particles, and fine drag particles.

In addition, the term "organic-inorganic hybrid fine particles" encompasses fine drag particles for drug delivery systems (DDS), fine particles for cosmetics, and organic-inorganic hybrid pigment fine particles.

An alkoxysilane compound may also be used as the film compound for fine particles other than fine nickel particles if they have active hydrogen groups, such as hydroxyl groups or amino groups, on their surfaces. Specific examples of such fine particles include metal oxides, such as alumina and lead oxide.

While the first and second film compounds used in this embodiment are film compounds having an epoxy group, they may be the same compound or different compounds. In addition, the first and second film compounds may have different functional groups. For example, one of the first or second films has an epoxy group while the other of the first or second films has an isocyanate group.

In the step D, the reactive glass substrate 41 (see FIGS. 1(A) and 1(B)) is prepared by bringing 2-methylimidazole into contact with the surface of the epoxidized glass substrate 14 (see FIG. 3(B)) to facilitate a coupling reaction between the epoxy group and an amino group, and then the epoxidized fine nickel particles 34 are bound to the surface of the reactive glass substrate 41 by bringing the epoxidized fine nickel particles 34 into contact with the surface of the reactive glass substrate 42 to form a bond through a coupling reaction between the epoxy group and an imino group, followed by removing unbound epoxidized fine nickel particles 24.

Bonds are formed between 2-methylimidazole, which has amino and imino groups at its 1- and 3-positions, respectively, and epoxy groups, with which they react, through the cross-linking reaction represented by Chemical Formula 6 below.

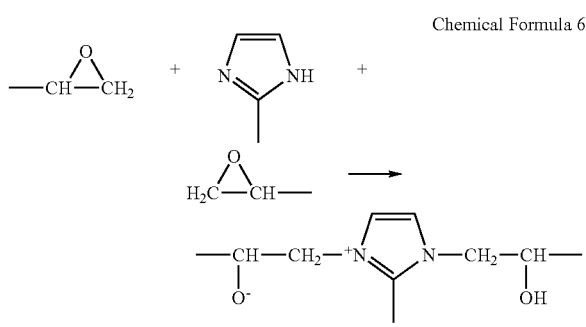

Chemical Formula 6

The reactive glass substrate 42 is produced by applying a reaction solution containing 2-methylimidazole and a solvent to the surface of the epoxidized glass substrate 14 and reacting them by heating. The application of the reaction solution may be performed by any method, such as doctor-blade coating, dip coating, spin coating, spraying, or screen printing.

The film precursor can be produced using any solvent in which 2-methylimidazole is soluble. For example, based on price, volatility at room temperature, and toxicity, lower alcohol solvents such as isopropyl alcohol and ethanol are preferred.

The amount of 2-methylimidazole added, the concentration of the solution applied, the reaction temperature, and the reaction time are appropriately adjusted depending on, for example, the types of substrate and fine particles used and the thickness of the fine particle film to be formed.

Figure 3:
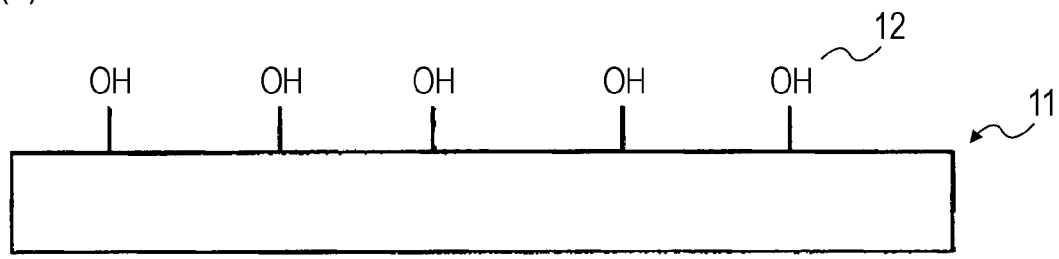
FIGS. 3(A) and 3(B) are a set of conceptual diagrams, enlarged to the molecular level, illustrating a step of producing an epoxidized glass substrate in methods for producing the patterned fine particle films.
Figure 3:
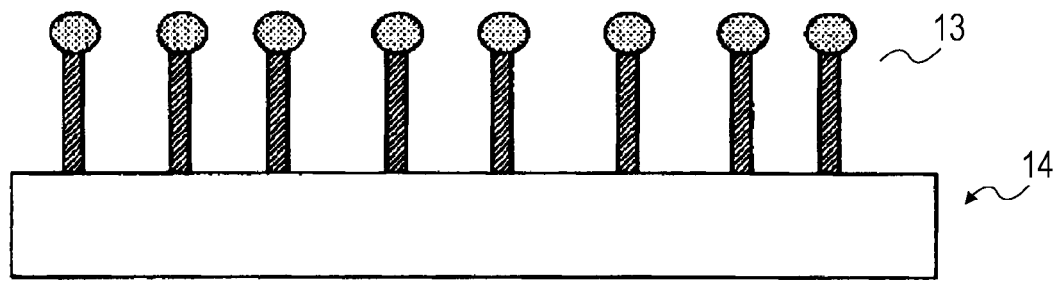
Figure 3:
Figure 4:
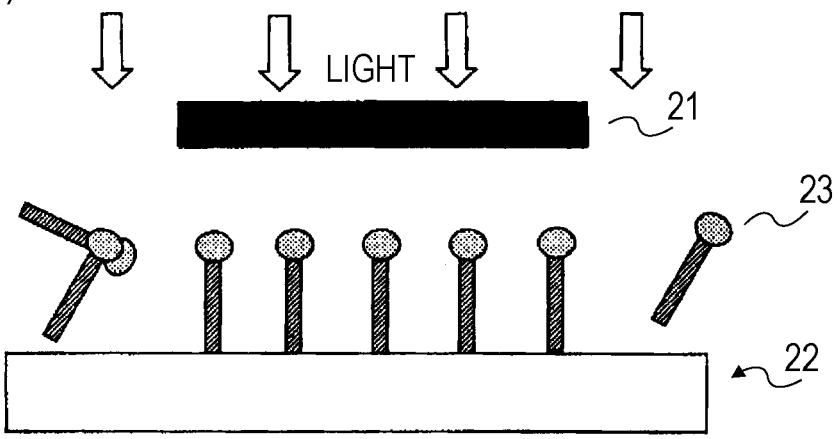
FIG. 4(A) is a conceptual diagram, enlarged to the molecular level, illustrating a step of performing patterning treatment in the methods for producing the patterned fine particle films.
FIG. 4(B) is a conceptual diagram, enlarged to the molecular level, illustrating a step of performing patterning treatment according to an embodiment.
Figure 4:
Figure 4:
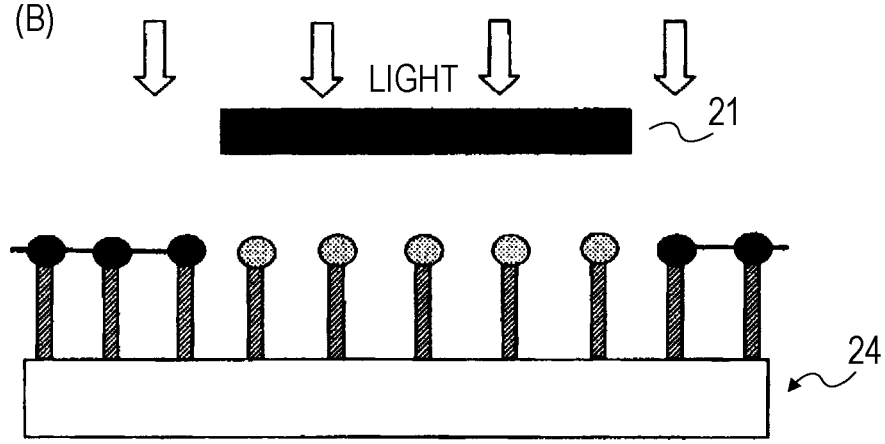
Figure 4:

After the reaction, the epoxidized glass substrate 14 is cleaned with a solvent to remove excess 2-methylimidazole remaining unreacted on the surface thereof so that the reactive glass substrate 41 is obtained (FIG. 3).

A dispersion of the epoxidized fine nickel particles 34 is applied to the surface of the reactive glass substrate 41 thus prepared and is heated to bind the epoxidized fine nickel particles 34 to the surface of the reactive glass substrate 41 through a coupling reaction between the epoxy groups on the epoxidized fine nickel particles 34 and the imino groups, derived from 2-methylimidazole, on the reactive glass substrate 41, thus producing a patterned single-layer fine particle film 1 (see FIG. 1) having a single fine particle layer.

In an embodiment, the heating temperature may be 100° C. to 200° C. If the heating temperature falls below 100° C., it takes an extended period of time for the coupling reaction to proceed. If the heating temperature exceeds 200° C., the monomolecular films 13 (see FIG. 3) having epoxy groups and the reactive monomolecular film 31 (see FIG. 5(A)) may undergo a decomposition reaction, thus making it impossible to obtain a uniform patterned single-layer fine particle film 1.

After the reaction, excess epoxidized fine nickel particles 34 are removed by cleaning with a solvent such as water or an alcohol.

While 2-methylimidazole is used as the coupling agent in this embodiment, any imidazole derivative represented by Chemical Formula 7 below may be used.

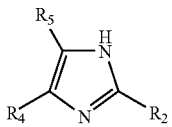

Chemical Formula 7

Specific examples of imidazole derivatives represented by Chemical Formula 7 include those shown in Items (31) to (38) below.
(31) 2-methylimidazole ($R_2$=Me, $R_4$=$R_5$=H)
(32) 2-undecylimidazole ($R_2$=$C_{11}H_{23}$, $R_4$=$R_5$=H)
(33) 2-pentadecylimidazole ($R_2$=$C_{15}H_{31}$, $R_4$=$R_5$=H)
(34) 2-methyl-4-ethylimidazole ($R_2$=Me, $R_4$=Et, $R_5$=H)
(35) 2-phenylimidazole ($R_2$=Ph, $R_4$=$R_5$=H)
(36) 2-phenyl-4-ethylimidazole ($R_2$=Ph, $R_4$=Et, $R_5$=H)
(37) 2-phenyl-4-methyl-5-hydroxymethylimidazole ($R_2$=Ph, $R_4$=Me, $R_5$=$CH_2OH$)
(38) 2-phenyl-4,5-bis(hydroxymethyl)imidazole ($R_2$=Ph, $R_4$=$R_5$=$CH_2OH$)
where Me, Et, and Ph denote methyl, ethyl, and phenyl groups, respectively.

The coupling agent used may also be a compound used as a curing agent for epoxy resin, for example, an acid anhydride such as phthalic anhydride or maleic anhydride, dicyandiamide, or a phenol derivative such as novolac. In this case, an imidazole derivative may be used as a catalyst to facilitate the coupling reaction.

In this embodiment, the case where a film compound having an epoxy group as a functional group is used is described. However, if a film compound having an amino or imino group as a functional group is used, a coupling agent having two or three or more epoxy groups or two or three or more isocyanate groups as coupling reactive groups is used. Specific examples of compounds having isocyanate groups include hexamethylene-1,6-diisocyanate, toluene-2,6-diisocyanate, and toluene-2,4-diisocyanate.

As in the case of 2-methylimidazole, the amount of diisocyanate compound added may be 5% to 15% by weight of the amount of epoxidized fine nickel particles. In this embodiment, the solvent that can be used to produce the film precursor is exemplified by an aromatic organic solvent such as xylene.

If a film compound having an imino or amino group is used, additionally, the cross-linking agent used may be a compound having two or three or more epoxy groups, for example, ethylene glycol diglycidyl ether.

In the step E, the epoxidized fine nickel particles 34 are prepared by bringing a solution containing an epoxidized alkoxysilane compound into contact with the surfaces of the fine nickel particles 31 to form a bond between alkoxysilyl groups and the hydroxyl groups 32 on the surfaces of the fine nickel particles 31, and then the reactive fine nickel particles 42 are prepared by bringing 2-methylimidazole into contact with the surfaces of the epoxidized fine nickel particles 34 so that they have films formed of 2-methylimidazole bound to the surfaces thereof by a bond formed through a coupling reaction between the epoxy group and the amino group derived from 2-methylimidazole.

The concentration of the 2-methylimidazole solution used, the reaction conditions, and so on are similar to those used in the preparation of the reactive glass substrate 41 in the step D except that, instead of applying the solution, the epoxidized fine nickel particles 34 are dispersed in the solution and heated. Therefore, a detailed description of the reactive fine nickel particles 42 will be omitted in the interest of brevity.

Other coupling agents that can be used are similar to those in the preparation of the reactive glass substrate 41 in the step D.

While the third film compound used in this embodiment is a film compound having an epoxy group, it may be the same compound as or different compounds from one or both of the first and second film compounds. In addition, the third film compound may have a functional group different from those of the first and second film compounds (for example, an amino group).

In the step F, the reactive fine nickel particles 42 are bound to the fine particle layer of the epoxidized fine nickel particles 34 by bringing the reactive fine nickel particles 42 into contact with the surface of the patterned single-layer fine particle film 1 or the patterned multilayer fine particle film 3, which includes the fine particle layer of the epoxidized fine nickel particles 24, to form a bond through a coupling reaction between the epoxy group and the imino group, followed by removing unbound reactive fine nickel particles 42.

In the step G, additionally, the epoxidized fine nickel particles 34 are bound to the fine particle layer of the reactive fine nickel particles 42 by bringing the epoxidized fine nickel particles 34 into contact with the surface of the patterned multilayer fine particle film 3, which includes the fine particle layer of the reactive fine nickel particles 42, to form a bond through a coupling reaction between the epoxy group and the imino group, followed by removing unbound epoxidized fine nickel particles 34.

The reaction conditions of the steps F and G are similar to those of the step E. Therefore, a detailed description of the reaction conditions for the steps F and G will be omitted in the interest of brevity.

While the preparation of a fine particle film including two fine particle layers has been described in this embodiment, a step H may be further carried out in which the steps F and G are repeated in that order to form a fine particle film including n fine particle layers (where n is an integer of two or more). The step H may be terminated either in the step F or in the step G.

Figure 2:
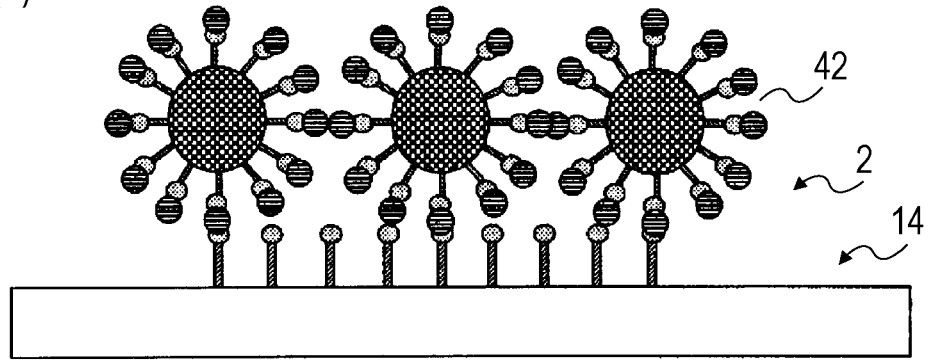
FIG. 2(A) is an illustrative diagram schematically showing the sectional structure of a patterned single-layer fine particle film according to a second embodiment.
FIG. 2(B) is an illustrative diagram schematically showing the sectional structure of a patterned multilayer fine particle film according to the same embodiment.
Figure 2:
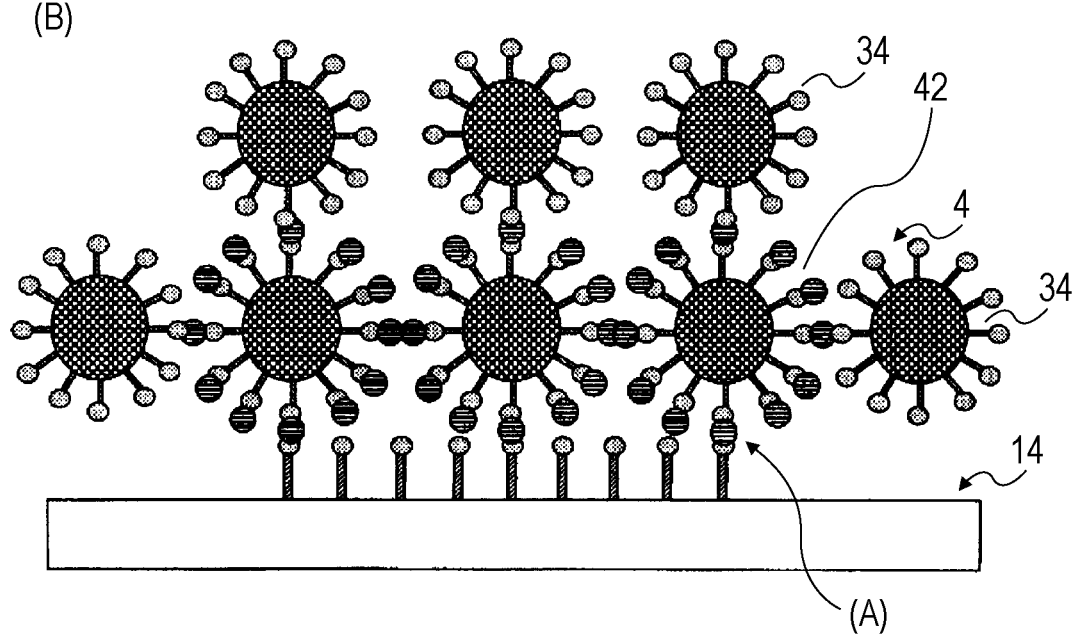

Referring to FIG. 2, a patterned single-layer fine particle film 2 and a patterned multilayer fine particle film 4 according to another embodiment will be described.

The patterned single-layer fine particle film 2 and the patterned multilayer fine particle film 4 include a fine particle layer in which the reactive fine nickel particles 42 are arranged and bound to the surface of the epoxidized glass substrate 14. In the patterned multilayer fine particle film 4, as shown in FIG. 2(B), the first to nth fine particle layers (where n is an integer of two or more; n=2 in this embodiment) are sequentially stacked in order from the epoxidized glass substrate 14 side to the air interface side.

The surface of the epoxidized glass substrate 14 is coated with the monomolecular film 13 of the film compound having an epoxy group.

The surfaces of the reactive fine nickel particles 42 forming the first fine particle layer are further coated with films of 2-methylimidazole bound by a bond formed through a coupling reaction between an amino group of 2-methylimidazole and an epoxy group.

The epoxidized glass substrate 14 and the reactive fine nickel particles 42 forming the first fine particle layer are bound to each other by a bond formed through a coupling reaction between the epoxy group and the amino or imino group of 2-methylimidazole; similarly, the reactive fine nickel particles 42 forming the odd-numbered fine particle layers and the epoxidized fine nickel particles 34 forming the even-numbered fine particle layers are bound to each other.

As shown in FIG. 2(B), the epoxidized fine nickel particles 34 can also be bound to the sides of the reactive fine nickel particles 42 of the odd-numbered layers, although FIG. 2(B) is drawn with the size of the fine particles exaggerated relative to that of the actual pattern for illustration purposes; they do not impair the shape of the pattern.

Referring to FIGS. 3(A), 3(B), FIGS. 4(A), 5(A), and 5(B), a method for producing the patterned single-layer fine particle film 2 and the patterned multilayer fine particle film 4 shown in FIGS. 2(A) and 2(B) includes a step A of preparing the epoxidized glass substrate 14 by bringing a solution containing an alkoxysilane compound having an epoxy group into contact with a surface of the glass substrate 11 to form a bond between alkoxysilyl groups and the hydroxyl groups 12 on the surface of the glass substrate 11. The method further includes a step B of preparing the patterned epoxidized glass substrate 22 (FIGS. 4(A) and 4(B)) through patterning treatment by selectively irradiating the surface of the epoxidized glass substrate 14 with light through the mask 21 covering the pattern region so that the epoxy group is selectively left only in the pattern region. The method also includes a step C of preparing the epoxidized fine nickel particles 34 by bringing an alkoxysilane compound having an epoxy group into contact with the surfaces of the fine nickel particles 31 to form a bond between alkoxysilyl groups and the hydroxyl groups 32 on the surfaces of the fine nickel particles 31 FIG. 5(A)). The method additionally includes a step D of preparing the reactive fine nickel particles 42 (FIGS. 2(A) and 2(B)) by bringing 2-methylimidazole into contact with the surfaces of the epoxidized fine nickel particles 34 to facilitate a coupling reaction between the epoxy group and an amino group, and then binding the reactive fine nickel particles 42 to the surface of the epoxidized glass substrate 14 by bringing the reactive fine nickel particles 42 into contact with the surface of the epoxidized glass substrate 14 to form a bond through a coupling reaction between the epoxy group and an imino group (an example of a second coupling reactive group), followed by removing unbound reactive fine nickel particles 42.

The method further includes a step E of preparing the epoxidized fine nickel particles 34 by bringing a solution containing an epoxidized alkoxysilane compound into contact with the surfaces of the fine nickel particles 31 to form a bond between alkoxysilyl groups and the hydroxyl groups 32 on the surfaces of the fine nickel particles 31. The method also includes a step F of binding the epoxidized fine nickel particles 34 to the fine particle layer of the reactive fine nickel particles 42 by bringing the epoxidized fine nickel particles 34 into contact with the surface of the patterned single-layer fine particle film 2 or the patterned multilayer fine particle film 4, which includes the fine particle layer of the reactive fine nickel particles 42, to form a bond through a coupling reaction between the epoxy group and the imino group, followed by removing unbound epoxidized fine nickel particles 34. The method additionally includes a step G of binding the reactive fine nickel particles 42 to the fine particle layer of the epoxidized fine nickel particles 34 by bringing the reactive fine nickel particles 42 into contact with the surface of the patterned multilayer fine particle film 4, which includes the fine particle layer of the epoxidized fine nickel particles 34, to form a bond through a coupling reaction between the epoxy group and the imino group, followed by removing unbound reactive fine nickel particles 42.

The preparation of the epoxidized glass substrate 14, the epoxidized fine nickel particles 34, the reactive glass substrate 41, and the reactive fine nickel particles 42 and the reactions thereof in the steps A to G are similar to those for the patterned single-layer fine particle film structure 1 and the patterned multilayer fine particle film structure 3 according to the various embodiments described with respect to FIGS. 1(A) and 1(B) and, therefore, a detailed description thereof will be omitted.

Example 1

Preparation of Epoxidized Glass Substrate

A glass substrate was prepared, cleaned, and sufficiently dried.

A reaction solution was prepared by weighing out 0.99 part by weight of 3-glycidoxypropyltrimethoxysilane (Chemical Formula 8, manufactured by Shin-Etsu Chemical Co., Ltd.) and 0.01 part by weight of dibutyltin bisacetylacetonate (condensation catalyst) and dissolving them in 100 parts by weight of hexamethyldisiloxane solvent. By this method, an epoxidized glass substrate could be prepared.

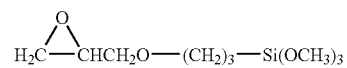

Chemical Formula 8

The reaction solution thus prepared was applied to the glass substrate and was left in air (relative humidity: 45%) to facilitate a reaction for about two hours.

Afterwards, the glass substrate was cleaned with chloroform to remove excess alkoxysilane compound and dibutyltin bisacetylacetonate.

Example 2

Preparation of Patterned Epoxidized Glass Substrate

The epoxidized glass substrate prepared in Example 1 was subjected to laser ablation by irradiation with a KrF excimer laser (wavelength: 248 nm; pulse width: 10 ns; laser intensity: 0.15 J/cm$^2$) through a mask (0.5 μm line-and-space) covering the pattern region to be formed to remove a monomolecular film, having epoxy groups, that covered the region other than the pattern region. By this method, a patterned epoxidized glass substrate was prepared.

A patterned epoxidized glass substrate could also be prepared by applying the cationic photopolymerization initiator Irgacure (registered trademark) 250 (a mixture of (4-methylphenyl)[4-(2-methylpropyl)phenyl]iodonium hexafluorophosphate) and propylene carbonate in a ratio of 3:1, manufactured by Ciba Specialty Chemicals plc) to the surface of the epoxidized glass substrate using MEK as a diluent and then irradiating it with far-ultraviolet rays through a mask similar to the above mask to facilitate a ring-opening polymerization of the epoxy groups of the monomolecular film that covered the region other than the pattern region.

Example 3

Preparation of Epoxidized Fine Nickel Particles

Anhydrous fine nickel particles with an average particle size of 30 nm were prepared and sufficiently dried.

A reaction solution was prepared by weighing out 0.99 part by weight of 3-glycidoxypropyltrimethoxysilane (Chemical Formula 8) and 0.01 part by weight of dibutyltin bisacetylacetonate (condensation catalyst) and dissolving them in 100 parts by weight of hexamethyldisiloxane solvent.

The reaction solution thus prepared was mixed with the fine nickel particles and was stirred in air (relative humidity: 45%) to facilitate a reaction for about two hours.

Afterwards, the fine nickel particles were cleaned with trichlene to remove excess alkoxysilane compound and dibutyltin bisacetylacetonate.

Example 4

Preparation of Patterned Reactive Glass Substrate

An ethanol solution of 2-methylimidazole was applied to the surface of the patterned epoxidized glass substrate prepared in Example 2 and was heated at 100° C. to facilitate a reaction between the epoxy group and the amino group of 2-methylimidazole, so that a patterned reactive glass substrate was obtained. Afterwards, the patterned reactive glass substrate could be cleaned with ethanol to remove excess 2-methylimidazole.

Example 5

Preparation of Reactive Fine Nickel Particles

The epoxidized fine nickel particles prepared in Example 3 were dispersed in an ethanol solution of 2-methylimidazole and were heated at 100° C. to facilitate a reaction between the epoxy group and the amino group of 2-methylimidazole so that reactive fine nickel particles were obtained. The reactive fine nickel particles could be cleaned with ethanol to remove excess 2-methylimidazole.

Example 6

Preparation of Patterned Fine Nickel Particle Film (1)

An ethanol dispersion of the epoxidized fine nickel particles prepared in Example 3 was applied to the surface of the reactive glass substrate prepared in Example 4 and was heated at 100° C. After the reaction, the reactive glass substrate was cleaned with water to remove excess epoxidized fine nickel particles.

An ethanol dispersion of the reactive fine nickel particles prepared in Example 5 was further applied to the surface of the patterned fine particle film thus prepared, which included a single fine particle layer, and was heated at 100° C. After the reaction, the patterned fine particle film was cleaned with water to remove excess reactive fine nickel particles so that a patterned fine particle film including two fine particle layers was obtained.

Example 7

Preparation of Patterned Fine Nickel Particle Film (2)

An ethanol dispersion of the reactive fine nickel particles prepared in Example 5 was applied to the surface of the patterned epoxidized glass substrate prepared in Example 2 and was heated at 100° C. After the reaction, the patterned epoxidized glass substrate was cleaned with water to remove excess reactive fine nickel particles.

An ethanol dispersion of the epoxidized fine nickel particles prepared in Example 3 was further applied to the surface of the patterned fine particle film thus prepared, which included a single fine particle layer, and was heated at 100° C.

After the reaction, the patterned fine particle film was cleaned with water to remove excess epoxidized fine nickel particles so that a patterned fine particle film including two fine particle layers was obtained.

Example 8

Preparation of Patterned Fine Nickel Particle Film (3)

The same processes as in Examples 1 and 3 were performed using a reaction solution prepared by weighing out 0.99 part by weight of 3-aminopropyltrimethoxysilane (Chemical Formula 9, manufactured by Shin-Etsu Chemical Co., Ltd.) and 0.01 part by weight of acetic acid (condensation catalyst) and dissolving them in 100 parts by weight of hexamethyldisiloxane-dimethylformamide mixed solvent (1:1 v/v) to prepare an aminated glass substrate and aminated fine nickel particles with a particle size of about 100 nm.

The aminated glass substrate was subjected to the same process as in Example 2 to prepare a patterned aminated glass substrate.

In addition, the same processes as in Examples 4 and 5 were performed using p-phenylene diisocyanate as a coupling agent to prepare a reactive glass substrate and reactive fine nickel particles having an isocyanate group as a coupling reactive group.

These materials were used to perform the same processes as in Examples 6 and 7, so that patterned fine particle films including one fine nickel particle layer (thickness: 100 nm) or two fine nickel particle layers (thickness: 200 nm) were obtained.

Chemical Formula 9

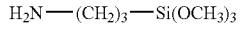

The invention claimed is:

1. A film structure, comprising:
   a substrate;
   a first alkoxysilane linker linked to the substrate through a first active hydrogen group of the substrate, the first alkoxysilane linker having a first epoxide reactant product;
   a fine particle;
   a second alkoxysilane linker linked to the particle through a second active hydrogen group of the particle, the second alkoxysilane linker having a second epoxide reactant product; and
   a coupling agent including an imidazole group linking the first alkoxysilane linker and the second alkoxysilane linker so as to link the particle to the substrate through the two alkoxysilane linkers and the coupling agent including the imidazole group disposed therebetween.

2. The film structure of claim 1, comprising a plurality of fine particles linked to the substrate to form a particle layer arranged into a pattern.

3. The film structure of claim 2, wherein the particle film includes a single particle layer.

4. The film structure of claim 1, further comprising:
   a second fine particle having one or more third active hydrogen groups;
   a third alkoxysilane linker linked to the second particle through the third active hydrogen group, said third alkoxysilane linker having a third epoxide reactant product; and a second coupling agent linking the second epoxide reactant product of the second alkoxysilane to the third epoxide reactant product of the third alkoxysilane thereby linking the second fine particle to the fine particle.

5. The film structure of claim 1, wherein the substrate includes a glass, lens, diffraction grating, metal, foil, aluminum, copper, silicon, semiconductor, electronic printed boards, passivation film, a capacitor, or combinations thereof.

6. The film structure of claim 1, wherein the one or more first and second active hydrogen groups include hydroxyl groups or amino groups.

7. The film structure of claim 1, wherein one or more of the alkoxysilane linkers include the epoxy reactant product formed from reacting an epoxy group with the coupling agent, and the coupling agent comprises 2-methylimidazole.

8. The film structure of claim 7, wherein a resulting structure linking the fine particle to the substrate includes the first alkoxysilane linker linked to the substrate, which is linked to the 2-methylimidazole reactant product, which is linked to the second alkoxysilane linker, which is linked to the particle so that the resulting linking structure includes two epoxy groups with the 2-methylimidazole reactant product disposed therebetween.

9. The film structure of claim 1, wherein the fine particles include at least one of:
- inorganic fine particles including a metal;
- inorganic fine particles including a metal oxide;
- organic fine particles including a polymer;
- organic fine particles including a polymer micelle; or
- organic-inorganic hybrid fine particles.

10. The film structure of claim 1, wherein the particle includes nickel.

* * * * *

UNITED STATES PATENT AND TRADEMARK OFFICE
CERTIFICATE OF CORRECTION

PATENT NO. : 8,568,862 B2  
APPLICATION NO. : 12/530553  
DATED : October 29, 2013  
INVENTOR(S) : Ogawa It is certified that error appears in the above-identified patent and that said Letters Patent is hereby corrected as shown below:

In the Specifications

In Column 1, Line 46, delete "films;" and insert -- films. --, therefor.

In Column 2, Line 59, delete "groups 31" and insert -- groups 32 --, therefor.

In Column 10, Line 2, delete "substrate 42" and insert -- substrate 41 --, therefor.

In Column 10, Line 24, delete "substrate 42" and insert -- substrate 41 --, therefor.

In Column 10, Line 59, delete "film 31" and insert -- film 33 --, therefor.

Signed and Sealed this  
Twenty-second Day of April, 2014

Michelle K. Lee  
*Deputy Director of the United States Patent and Trademark Office*